US006254612B1

(12) United States Patent
Hieshima

(10) Patent No.: US 6,254,612 B1
(45) Date of Patent: *Jul. 3, 2001

(54) HYDRAULIC STENT DEPLOYMENT SYSTEM

(75) Inventor: Grant Hieshima, Huntington Beach, CA (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/382,967

(22) Filed: Aug. 25, 1999

Related U.S. Application Data

(63) Continuation-in-part of application No. 09/177,848, filed on Oct. 22, 1998.

(51) Int. Cl.[7] ............................................. A61F 11/00
(52) U.S. Cl. ......................................................... 606/108
(58) Field of Search ............................... 606/108, 200, 606/191, 198, 194, 206, 1; 623/1, 12

(56) References Cited

U.S. PATENT DOCUMENTS

| | | |
|---|---|---|
| 2,853,070 | 9/1958 | Julliard . |
| 3,353,718 | 11/1967 | McLay . |
| 4,512,338 | 4/1985 | Balko et al. . |
| 4,743,230 | 5/1988 | Nordquest . |
| 4,832,692 | 5/1989 | Box et al. . |
| 4,919,121 | 4/1990 | Rydell et al. . |
| 4,994,069 | 2/1991 | Ritchart et al. . |
| 4,994,071 | 2/1991 | MacGregor . |
| 5,108,407 | 4/1992 | Geremia et al. . |
| 5,122,136 | 6/1992 | Guglielmi et al. . |
| 5,137,514 | 8/1992 | Ryan . |
| 5,167,624 | 12/1992 | Butler et al. . |
| 5,168,757 | 12/1992 | Rabenau et al. . |
| 5,234,437 | 8/1993 | Sepetka . |
| 5,250,071 | 10/1993 | Palermo . |
| 5,261,916 | 11/1993 | Engelson . |
| 5,263,964 | 11/1993 | Purdy . |
| 5,304,195 | 4/1994 | Twyford, Jr. et al. . |
| 5,312,415 | 5/1994 | Palermo . |
| 5,334,210 | 8/1994 | Gianturco . |
| 5,336,183 | 8/1994 | Greelis et al. . |
| 5,342,304 | 8/1994 | Tacklind et al. . |
| 5,350,397 | 9/1994 | Palermo et al. . |

(List continued on next page.)

FOREIGN PATENT DOCUMENTS

| | | |
|---|---|---|
| 0 717 969 | 6/1996 | (EP) . |
| WO 98/02100 | 1/1998 | (WO) . |

OTHER PUBLICATIONS

Brochure entitled, "Guglielmi Detachable Coils," by Boston Scientific.
Label of IDC–18 Interlocking Detachable Coil by Target Therapeutics, Inc.
Brochure entitled, "Detachable Coil System," by Cook.
Brochure entitled, "Basix25™ Inflation Device," by Merit Medical Systems, Inc.
Brochure entitled, "MonarchAP® Inflation Device," by Merit Medical Systems, Inc.
Label of B. Braun Inflation Device Kit by B. Braun Medical Inc.

*Primary Examiner*—Kevin Truong
(74) *Attorney, Agent, or Firm*—Henry W. Collins

(57) ABSTRACT

The present invention relates to a medical device for placing an intravascular stent at a preselected location within a vessel of the human body, and more particularly, relates to a catheter having a distal tip for retaining the stent in order to transport the stent to a preselected position within the vessel and a control mechanism for releasing the stent at the preselected position.

18 Claims, 3 Drawing Sheets

U.S. PATENT DOCUMENTS

| | | |
|---|---|---|
| 5,382,259 | 1/1995 | Phelps et al. . |
| 5,403,292 | 4/1995 | Ju . |
| 5,443,478 | 8/1995 | Purdy . |
| 5,470,317 | 11/1995 | Cananzey et al. . |
| 5,551,954 | 9/1996 | Buscemi . |
| 5,578,074 | 11/1996 | Mirigian . |
| 5,582,619 | 12/1996 | Ken . |
| 5,601,600 | 2/1997 | Ton . |
| 5,609,608 | 3/1997 | Benett et al. . |
| 5,647,847 | 7/1997 | Lafontaine et al. . |
| 5,690,667 | 11/1997 | Gia . |
| 5,772,668 | 6/1998 | Summers . |
| 5,853,418 | 12/1998 | Ken et al. . |
| 5,928,226 * | 7/1999 | Guglielmi et al. .................... 606/108 |
| 5,984,929 * | 11/1999 | Bashiri et al. ........................ 606/108 |

* cited by examiner

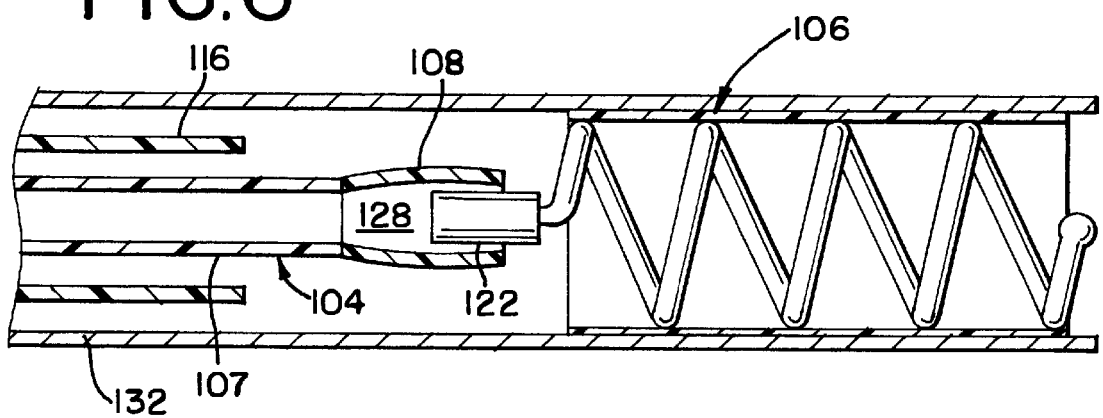
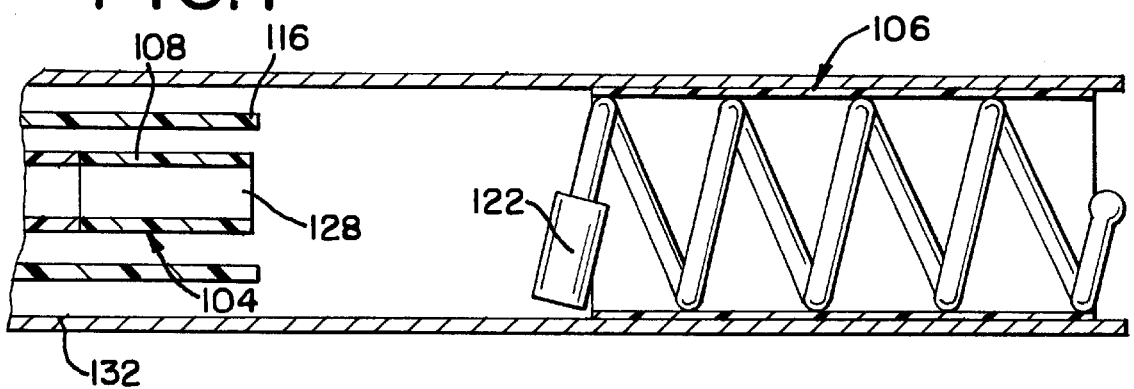

HYDRAULIC STENT DEPLOYMENT SYSTEM

The application is a continuation-in-part of U.S. patent application Ser. No. 09/177,848, filed on Oct. 22, 1998, now pending and entitled, "Embolic Coil Hydraulic Deployment System," which is incorporated herein by reference.

BACKGROUND OF THE INVENTION

1. Field of the Invention

The present invention relates to a medical device for placing an intravascular stent at a preselected location within a vessel of the human body, and more particularly, relates to a catheter having a distal tip for retaining the stent in order to transport the stent to a preselected position within the vessel and a control mechanism for releasing the stent at the preselected position.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled, "A Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering an embolic coil to a preselected position within a vessel of the human body in order to treat aneurysms or alternatively to occlude the blood vessel at the particular location.

Stents which are placed in vessels may take the form of helically wound wire, or tubular like structures with numerous patterns defining the walls of the tubule. Examples of various stent configurations are disclosed in U.S. Pat. No. 4,512,338, entitled, "Process for Restoring Patentcy to Body Vessels"; U.S. Pat. No. 5,551,954, entitled, "Biodegradable Drug Delivery Vascular Stent"; and U.S. Pat. No. 4,994,071, entitled, "Bifurcating Stent Apparatus and Method." Stents are generally formed of materials that can retain their shape under the pulsatile flow conditions encountered when placed within the body vessel. Some materials that have been used to make stents include metals and alloys, such as, stainless steel, tantalum, tungsten and nitinol, as well as polymers such as polyvinyl alcohol (PVA), polyglycolic acid (PGA) and collagen. On occasion multiple stents are placed at a given location to provide the desired vascular support.

In the past, the deployment of stents has been accomplished by numerous techniques. One such technique used to deploy a typical wire stent uses a pusher wire to push the wire stent through the lumen of a properly positioned cannula. As the stent exits the cannula it takes a predetermined shape until completely deposited in the vessel. This procedure is usually conducted under fluoroscopic visualization, such that the movement of the stent through the vasculature can be monitored. With these placements systems there is very little control over the exact placement of the stent since the stent may be ejected to a position some distance beyond the end of the cannula. As is apparent, with these latter systems, when the stent has been released from the cannula it is difficult, if not impossible, to retrieve the stent or to reposition the stent.

Numerous procedures have been developed to enable more accurate positioning of stents within a vessel. One such procedure utilizes a helically wound wire loop stent with a relaxed diameter. The stent is wound on a smaller diameter delivery while fixing the ends of the stent. This keeps the stent in a small diameter, tightly wound coil. This system is then delivered through the lumen of a properly positioned catheter exiting at a desired location. Once the delivery wire is activated to release the ends of the stent, the stent radially expands to its relaxed larger diameter. Such a stent positioning method is disclosed in U.S. Pat. No. 5,772,668, entitled, "Apparatus for Placing an Endoprosthesis."

Another stent positioning system utilizes a self expanding tubular stent. This stent has a relaxed diameter that approximates the diameter of the vessel to be supported. For transport through the catheter, the stent is positioned on a smaller diameter delivery wire. A sheath is positioned over the stent/delivery wire assembly constraining the stent to a smaller diameter. Once the assembly is placed at the desired location in the vasculature, the sheath is withdrawn exposing the stent allowing the stent to return to its predetermined larger size. The expansion of the stent uncouples the stent from the delivery wire while depositing the stent in the vessel at the desired location.

Another stent positioning system utilizes a radially expandable tubular stent formed of a malleable material. This tubular stent has a predetermined expanded diameter defining a lumen that is approximately the same diameter as the vessel to which the stent will be placed. A balloon catheter is placed within the lumen of the stent and the stent is subsequently compressed to a smaller diameter on top of the balloon portion of the catheter. The assembly is then placed within a properly positioned catheter and delivered to the desired location. Inflating the balloon thereby expanding the diameter of the compressed stent deploys the stent. Once the stent is expanded to its predetermined diameter the balloon is deflated and removed leaving the stent deposited at the desired location.

SUMMARY OF THE INVENTION

The present invention is directed toward an intravascular stent deployment system for use in placing a stent at a preselected site within a vessel which includes an elongated, flexible catheter having a distal section for retaining the stent so that the stent may be moved to the preselected position within the vessel. The catheter has a lumen which extends therethrough the length of the catheter and also includes a distal section which is formed of a material having a durometer such that when a fluid pressure of about 300 pounds per square inch (psi) is applied to the interior of the catheter, the walls of the distal tip expand outwardly, or radially, to thereby increase the lumen of the distal section of the catheter. The headpiece element of the stent is placed into the lumen of the distal section of the catheter and is retained by the distal section of the catheter. A hydraulic injector, such as a syringe, is coupled to the proximal section of the catheter for applying a fluid pressure to the interior of the catheter. When the stent is placed at a desired position within a vessel, fluid pressure is then applied to the interior of the catheter by the hydraulic injector to thereby cause the walls of the distal section to expand outwardly to thereby release the stent for placement in the vessel.

In accordance with another aspect of the present invention, the flexible catheter is comprised of a proximal section and a relatively short distal section. The proximal section is formed of a material which is sufficiently flexible to be passed through the vasculature of the human body and is of a durometer which essentially resists outward expansion when a fluid pressure on the order of about 300 psi is applied to the interior of the catheter. The distal section of the catheter is formed of a material which is also sufficiently flexible to be passed through the vasculature of the body, yet is of a durometer which is significantly lower than the durometer of the proximal section and exhibits the property of expanding outwardly, or radially, when such a fluid pressure is applied to the interior of the catheter to thereby permit the release of the stent.

In accordance with still another aspect of the present invention, the distal section of the catheter has a durometer in a range of between about 25 D and 55 D.

In still another aspect of the present invention, the stent is comprised of a proximal end and a distal section. The proximal end of the stent is disposed in a fluid-tight engagement within the lumen of the distal section of the catheter and is retained by the lumen of the catheter for subsequent release.

In another aspect of the present invention, the hydraulic injector for applying a fluid pressure to the interior of the catheter takes the form of a syringe which is coupled to the proximal section of the catheter for, upon movement of the piston, creating a fluid pressure which is applied to the interior of the catheter to thereby cause the release of the stent.

In another aspect of the present invention the stent is comprised of a headpiece element with a coil that extends from the headpiece and a covering that extends over the periphery of the coil. The cover may be a simple covering attached at one end or may take the form of a cover as described in U.S. patent application Ser. No. 09/052,402, filed on Mar. 31, 1998, entitled, "Stent Aneurysm Treatment System and Method" and assigned to the same assignee as the present application. The material used in making the cover may be elastic in nature allowing it to be elongated for delivery through or relatively inelastic in which case the cover would be folded or compressed for delivery through a properly positioned catheter. Suitable materials for such cover include metals such as nitinol or polymers such as polyether block amides, nylons, polyesters or polyurethanes or composites of any of these or other materials.

In accordance with another aspect of the present invention, the stent may take the form of other types of implantable devices, such as a vascular filter.

In another aspect of the present invention, there is provided a method for placing a stent at a selected site within a vessel of the body comprising the steps of advancing a catheter through the vasculature of the body to place a stent which is retained within the lumen of the distal tip of the catheter to a preselected site, applying a fluid pressure to the interior of the catheter to thereby cause the distal tip of the catheter to expand radially outwardly to release the stent at the preselected site, and withdrawing the catheter from the vasculature system.

These aspects of the invention and the advantages thereof will be more clearly understood from the following description and drawings of a preferred embodiment of the present invention:

BRIEF DESCRIPTION OF THE DRAWINGS

FIGS. 4 through 6 illustrate the sequential steps in the radial expansion of the distal tip of the stent deployment system as the stent is released; and, FIG. 7 illustrates the distal tip of the stent deployment system after release of the stent.

DESCRIPTION OF A PREFERRED EMBODIMENT

Figure 1:
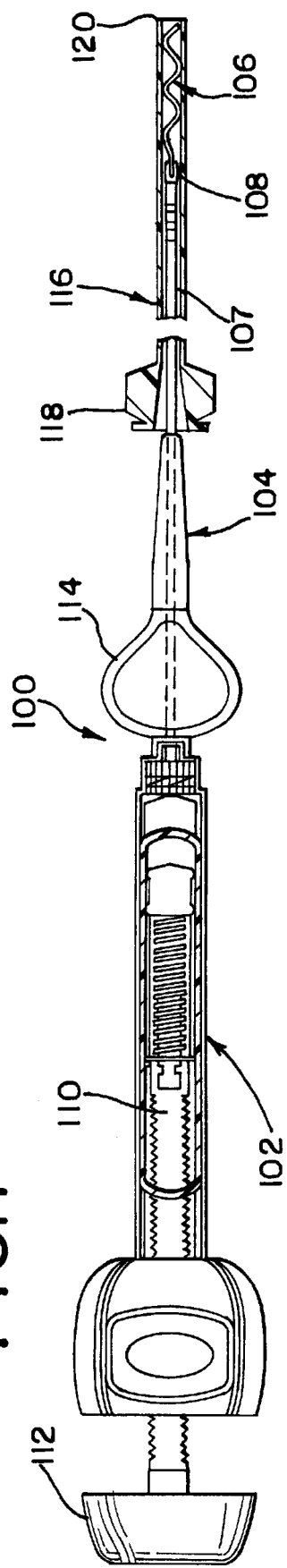
FIG. 1 is an enlarged partially sectioned view of the hydraulic stent deployment system of the present invention.

FIG. 1 generally illustrates the intravascular stent deployment system 100 which is comprised of a hydraulic injector or syringe 102, coupled to the proximal end of a catheter 104. A stent 106 is disposed within the lumen of the distal section 108 of the catheter 104. The proximal end of the stent 106 is tightly held within the lumen of the distal section 108 of the catheter 104 until the deployment system is activated for release of the stent. As may be seen, the syringe 102 includes a threaded piston 110 which is controlled by a handle 112 for infusing fluid into the interior of the catheter 104. Also as illustrated, the catheter 104 includes a winged hub 114 which aids in the insertion of the catheter into the access catheter 116 which has a proximal hub 118 that is placed in the vascular system of the body.

Figure 2:
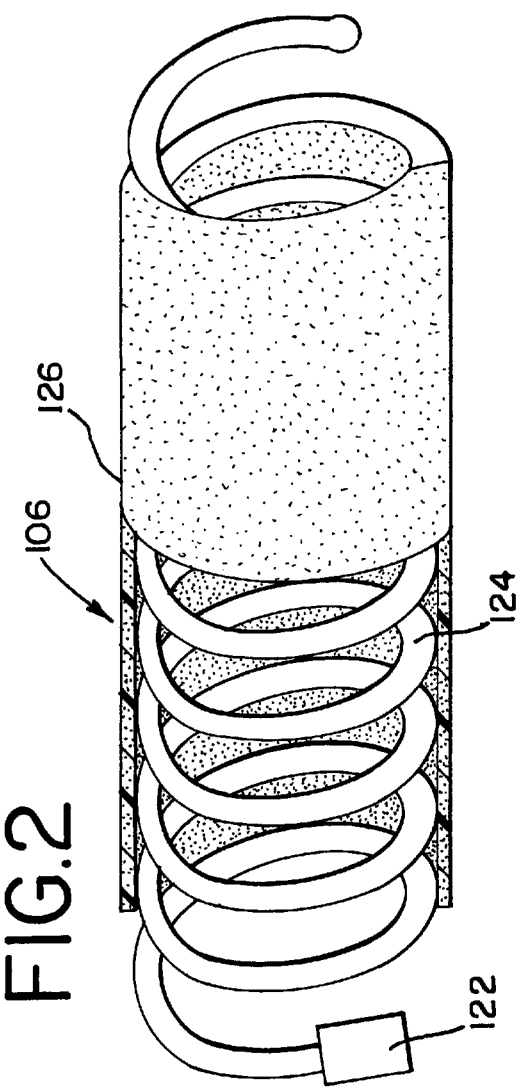
FIG. 2 is an enlarged partially sectioned view showing the stent of the present invention.

FIG. 2 illustrates in more detail an alternate embodiment of the stent 106. The stent 106 is comprised of a headpiece element 122 attached to a coil 124 and a cover 126 which is placed over and attached to the coil 124. The coil 124 is made of a wire formed into a helical shape with some predetermined pitch and diameter to fit the desired vasculature. The coil 124 is preferably made from a super elastic material such as nitinol, however any material that would allow the coil 124 to be extended to an elongated configuration and return to a relaxed helical configuration is suitable.

Figure 3:
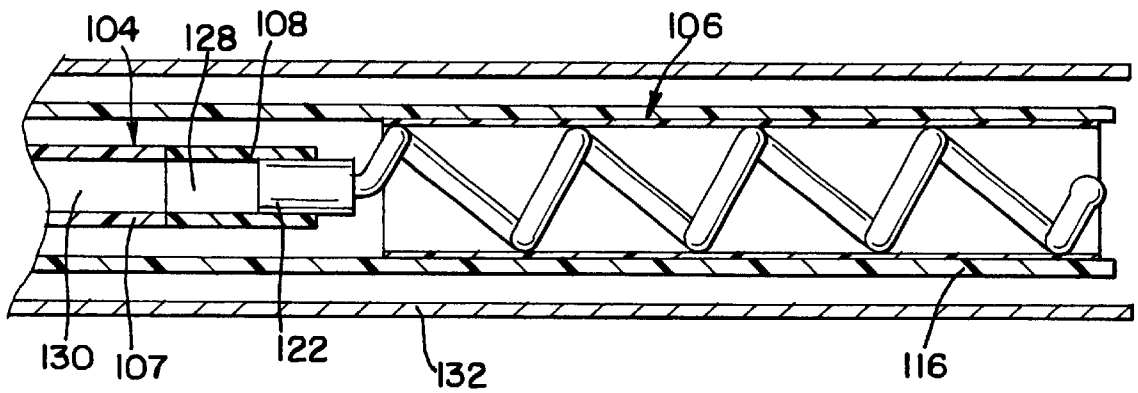
FIG. 3 is an enlarged partially sectioned view showing the distal end of the stent deployment system prior to deployment of the stent in the vasculature.

FIG. 3 illustrates in more detail the distal end of the catheter 104. The catheter 104 includes a proximal section 107 and the distal section 108. The headpiece element 122 of the stent 106 is disposed within the distal section 108 of the catheter 104 and is tightly held within the lumen 128 of this distal section 108 prior to release of the stent 106. As may be appreciated, FIG. 3 illustrates the stent deployment system 100 prior to activation of the piston of the syringe 102 and prior to release of the stent 106 while located in access catheter 116 located within vessel 132.

The stent 106 may take various forms and configurations and may even take the form of a headpiece element attached to a loop of wire connected to a mesh material connected to another loop of wire. As in all configurations of stent 106 and specifically with the configuration of stent 106 as illustrated in FIG. 3, the headpiece element 122 provides a location of attachment between the stent 106 and the distal end of the catheter 104.

Preferably, the proximal section 107 and the distal section 108 of the catheter 104 are formed of materials having different durometers. The proximal section 107 is preferably formed of Pebax material having a durometer in a range of about 62 D to 75 D. The proximal section is sufficiently flexible to transverse the vasculature of the human body, but is sufficiently rigid such that when a fluid pressure of approximately 300 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 300 psi is applied to the interior of the catheter the walls of the distal section 108 expand radially, somewhat similar to the action of a balloon inflating, to thereby release the headpiece element 122 of the stent 106. As may be appreciated, there are numerous materials which could be used to fabricate the proximal section 107 and distal section 108 of the catheter 104, however, the distal section 108 is preferably formed from a block copolymer such as Pebax having a durometer of between 25 D and 55 D with a durometer of 40 D being the preferred durometer.

Figure 4:
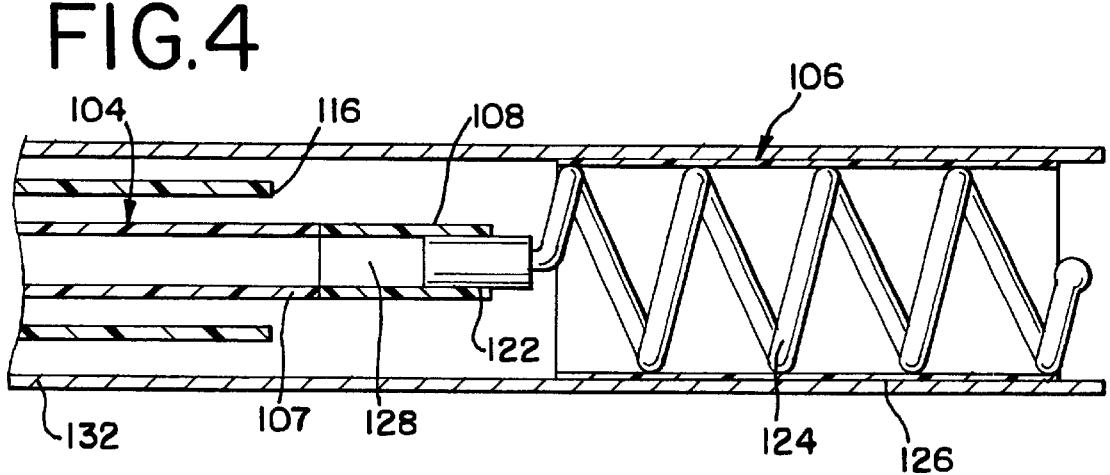
Figure 5:
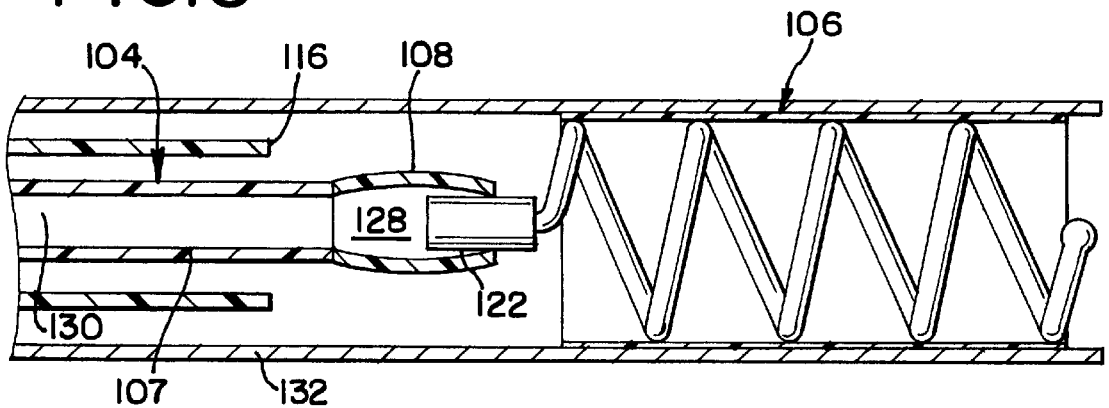

FIGS. 4 through 6 generally illustrate the stent 106 release mechanism in action for the intravascular stent deployment system 100. More particularly, as shown in FIG. 4, when a hydraulic pressure is applied to the interior 130 of the catheter 104 the relatively low durometer distal section 108 of the catheter 104 begins to expand radially, much as a balloon expands during the process of inflation. As the distal section 108 continues to expand radially there comes a point as illustrated in FIG. 6 in which the stent 106 becomes disengaged from the lumen 128 of the distal section 108 and the stent is then released from the catheter 104 and is deployed at that location within the vessel 132.

As illustrated in FIG. 7, when the stent 106 has been released from the catheter 104, the catheter may then be withdrawn leaving the stent positioned at the desired site.

With the intravascular stent deployment system of the present invention it is possible to place a stent very precisely at a desired location within a vessel. Once the stent has been placed in that location by use of the catheter 104, the catheter may be activated by applying a hydraulic pressure to the interior of the catheter to thereby cause the catheter to release the stent 106 and deposit the stent 106 very accurately at the desired location.

As is apparent, there are numerous modifications of the preferred embodiment described above which will be readily apparent to one skilled in the art, such as many variations and modifications of the stent including numerous stent winding configurations, or alternatively other types of implant devices, such as a vascular filter. Also, there are obvious variations of the syringe arrangement for applying a fluid pressure to the interior of the catheter, including many other fluid pressure generating systems for increasing the pressure within the interior of a catheter in order to cause the distal section of the catheter to expand. These modifications would be apparent to those having ordinary skill in the art to which this invention relates and are intended to be within the scope of the claims, which follow:

That which is claimed is:

1. A stent deployment system for use in placing a stent at a preselected site within a vessel comprising:

an elongate flexible catheter having a lumen extending therethrough and having a proximal section and a distal section, the distal section of the catheter being formed of a material having a durometer which exhibits the characteristic that when a fluid pressure is applied to the interior of the catheter the walls of the distal section of the catheter expand outwardly;

a stent comprised of a headpiece element and a coil coupled to and extending from said headpiece, said headpiece of said stent being disposed in and in fluid-tight engagement with the lumen of the distal section of the catheter; and, a syringe coupled to the proximal section of the catheter for applying a fluid pressure to the interior of the catheter to thereby cause the distal section of the catheter to expand outwardly to release the headpiece of said stent to thereby deposit said stent at a preselected site.

2. A stent deployment system as defined in claim 1, wherein said stent includes a covering which extends around the periphery of the coil.

3. A stent deployment system as defined in claim 2, wherein said coil is formed of a flexible resilient wire formed into a helical configuration.

4. A stent deployment system as defined in claim 2, wherein said coil is comprised of a shape memory material.

5. The stent deployment system as defined in claim 2, wherein said coil is formed of a radiopaque material.

6. The stent deployment system as defined in claim 2, wherein said coil is comprised of nitinol.

7. A stent deployment system for use in placing a stent at a preselected site within a vessel comprising:

an elongate flexible catheter having a lumen extending therethrough and having a proximal section and a distal section, the distal section of the catheter being formed of a material having a durometer which exhibits the characteristic that when a fluid pressure is applied to the interior of the catheter the walls of the distal section of the catheter expand outwardly;

a stent system comprised of a headpiece element and a stent body element coupled to and extending from said headpiece, said headpiece being disposed in and in fluid-tight engagement with the lumen of the distal section of the catheter; and, a syringe coupled to the proximal section of the catheter for applying a fluid pressure to the interior of the catheter to thereby cause the distal section of the catheter to expand outwardly to release the headpiece of said stent to thereby deposit said stent system at a preselected site.

8. A stent deployment system as defined in claim 7, wherein said stent body element includes a covering.

9. A stent deployment system as defined in claim 8, wherein said stent body element is formed of a shape memory material.

10. A stent deployment system as defined in claim 8, wherein said stent body element comprises of nitinol.

11. A stent deployment system as defined in claim 8, wherein said stent body element comprises a radiopaque material.

12. A stent deployment system for use in placing a stent at a preselected site within a vessel comprising:

an elongate flexible catheter having a lumen extending therethrough and having a proximal section and a distal section, the distal section of the catheter being formed of a material having a durometer which exhibits the characteristic that when a fluid pressure is applied to the interior of the catheter the walls of the distal section of the catheter expand outwardly, a stent system comprised of a coil having a proximal end and a distal section and said proximal end being disposed in fluid-tight engagement within the lumen of the distal section of the catheter; and, a syringe coupled to the proximal section of the catheter for applying a fluid pressure to the interior of the catheter to thereby cause the distal section of the catheter to expand outwardly to release the proximal end of said stent to thereby deposit said stent at a preselected site.

13. A stent deployment system as defined in claim 12, wherein said stent includes a covering.

14. The stent deployment system as defined in claim 13, wherein said distal section of said coil is comprised of a helically shaped wire.

15. The stent deployment system as defined in claim 14, wherein said helically shaped wire is formed of a shape memory material.

16. The stent deployment system as defined in claim 14, wherein said helically shaped wire is formed of nitinol.

17. The stent deployment system as defined in claim 12, wherein said stent system is comprised of a radiopaque material.

18. The stent deployment system as defined in claim 12, wherein said distal section of said coil is comprised of a mesh.

* * * * *